(12) United States Patent
Lukas et al.

(10) Patent No.: US 12,214,608 B2
(45) Date of Patent: Feb. 4, 2025

(54) METHODS AND SYSTEMS FOR LASER MARKING PHARMACEUTICAL CAPSULES DURING MANUFACTURING

(71) Applicant: TECHNOPHAR EQUIPMENT AND SERVICE (2007) LTD.

(72) Inventors: Paul Lukas, Harrow (CA); Stelian Ursachi, Belle River (CA); Thomas Stecko, Tecumseh (CA)

(73) Assignee: TECHNOPHAR EQUIPMENT AND SERVICE (2007) LTD., Windsor (CA)

( * ) Notice: Subject to any disclaimer, the term of this patent is extended or adjusted under 35 U.S.C. 154(b) by 1212 days.

(21) Appl. No.: 16/783,506

(22) Filed: Feb. 6, 2020

(65) Prior Publication Data

US 2020/0346477 A1 Nov. 5, 2020

Related U.S. Application Data

(60) Provisional application No. 62/841,393, filed on May 1, 2019.

(51) Int. Cl.
*A61J 3/00* (2006.01)
*A61J 3/07* (2006.01)
*A61K 9/20* (2006.01)
*B29C 67/00* (2017.01)
*B41F 17/36* (2006.01)
*B41M 5/26* (2006.01)

(52) U.S. Cl.
CPC ............... *B41M 5/26* (2013.01); *A61J 3/007* (2013.01); *A61K 9/2072* (2013.01); *B29C 67/0003* (2013.01)

(58) Field of Classification Search
CPC ....... B29C 67/0003; B41M 5/26; A61J 3/007; A61L 9/2072
See application file for complete search history.

(56) References Cited

U.S. PATENT DOCUMENTS

| | | | | | |
|---|---|---|---|---|---|
| 2,152,101 | A | * | 3/1939 | Scherer | B29C 51/225 264/DIG. 37 |
| 2,334,600 | A | * | 11/1943 | Boysen | A61J 3/07 206/532 |
| 2,497,212 | A | * | 2/1950 | Donofrio | B29C 51/445 425/513 |
| 4,567,714 | A | * | 2/1986 | Chasman | A61J 3/07 53/529 |

(Continued)

FOREIGN PATENT DOCUMENTS

| | | | | | |
|---|---|---|---|---|---|
| JP | 2011120619 | A | * | 6/2011 | ............... A61J 3/07 |
| WO | WO-0028976 | A1 | * | 5/2000 | ............... A61J 1/067 |

OTHER PUBLICATIONS

First Office Action received for Canadian Application No. 3,069,207 dated Mar. 3, 2021.

(Continued)

*Primary Examiner* — Thomas M Wittenschlaeger
*Assistant Examiner* — David G Shutty
(74) *Attorney, Agent, or Firm* — Greer, Burns & Crain, Ltd

(57) ABSTRACT

A method is provided for applying a laser marking to a sheet of material forming a capsule from portions of the sheet of material using a pair of die rollers wherein the location of the laser marking is established such that it does not overlap at least one of a seal between the pair of sheets of material formed during the formation of the capsule.

11 Claims, 12 Drawing Sheets

(56) References Cited

U.S. PATENT DOCUMENTS

| | | | | |
|---|---|---|---|---|
| 5,246,635 | A * | 9/1993 | Ratko | B29C 43/222 |
| | | | | 425/804 |
| 5,740,660 | A * | 4/1998 | Rowe | B65B 9/023 |
| | | | | 53/454 |
| 5,761,886 | A * | 6/1998 | Parkhideh | A61J 3/07 |
| | | | | 53/140 |
| 6,429,889 | B1 * | 8/2002 | Murokh | B41M 5/26 |
| | | | | 219/121.6 |
| 6,574,945 | B2 * | 6/2003 | Martinez, Jr. | B65B 29/10 |
| | | | | 53/239 |
| 6,769,226 | B2 * | 8/2004 | Holland | A61J 3/07 |
| | | | | 53/64 |
| 6,776,340 | B2 * | 8/2004 | Murokh | G06Q 20/203 |
| | | | | 705/28 |
| 6,884,060 | B2 * | 4/2005 | Tanner | A61K 9/4833 |
| | | | | 425/224 |
| 6,935,090 | B2 * | 8/2005 | Stolz | A61J 3/07 |
| | | | | 53/433 |
| 7,490,456 | B2 * | 2/2009 | Draisey | B65B 61/00 |
| | | | | 53/DIG. 2 |
| 8,739,698 | B2 * | 6/2014 | Salazar | A61J 3/07 |
| | | | | 101/37 |
| 8,967,989 | B2 * | 3/2015 | Altamar | A61J 3/07 |
| | | | | 424/408 |
| 8,974,820 | B2 * | 3/2015 | Altamar | A61K 9/4808 |
| | | | | 424/458 |
| 11,793,724 | B2 * | 10/2023 | Jung | B41F 17/36 |
| 2002/0026771 | A1 * | 3/2002 | Brown | A61K 8/11 |
| | | | | 53/454 |
| 2003/0014946 | A1 * | 1/2003 | Steele | B65B 9/042 |
| | | | | 53/454 |
| 2010/0018170 | A1 * | 1/2010 | Oana | A61J 3/07 |
| | | | | 53/563 |
| 2010/0140830 | A1 * | 6/2010 | Perrone | A61J 3/07 |
| | | | | 264/153 |
| 2020/0054526 | A1 * | 2/2020 | Jung | A61J 3/077 |
| 2020/0346477 | A1 * | 11/2020 | Lukas | B41M 5/26 |
| 2021/0213726 | A1 * | 7/2021 | Tanaka | B41J 3/407 |
| 2022/0175617 | A1 * | 6/2022 | Murokh | B23K 26/032 |

OTHER PUBLICATIONS

Second Office Action received for Canadian Application No. 3,069,207 dated Aug. 20, 2021.

* cited by examiner

METHODS AND SYSTEMS FOR LASER MARKING PHARMACEUTICAL CAPSULES DURING MANUFACTURING

RELATED APPLICATION

The present application is a Non-Provisional of, and claims 35 USC 119 priority from, U.S. Provisional Application Ser. No. 62/841,393 filed May 1, 2019, the contents of which are incorporated by reference herein.

FIELD OF THE INVENTION

This patent application relates to softgel capsule manufacturing and more specifically to laser marking softgel capsules and encapsulated softgel capsules using gelatin, non-animal gelatin, tapioca starch, carrageenan, pea starch, and polymers during manufacturing.

BACKGROUND

Multiple requirements such as quality control, quality assurance, product branding, and regulatory requirements lead to it being necessary to mark a wide range of products including, but not limited to, pharmaceutical products such as capsules, tablets etc. with markings which may include, for example letters, pictures, marks, symbols, figures, logos, and machine readable codes, e.g. two-dimensional (2D) bar codes.

Amongst these products and specifically pharmaceutical products are what are known as soft-gel (or softgel) capsules which are an oral dosage form for medicines similar to capsules which consist of a shell surrounding a liquid filler. Prior art softgel shells are formed with a combination of gelatin, water, an opacifier and a plasticizer such as glycerin or sorbitol, for example. The softgel capsules are produced in a process known as encapsulation using the Rotary Die Encapsulation which is best described as a form/fill/seal process. Two flat ribbons of shell material are manufactured and brought together on a twin set of rotating dies which contain recesses in the desired size and shape, cut out the ribbons and form a seal around the outside. At the same time a pump delivers a precise dose of fill material through a nozzle incorporated into a filling wedge whose tip sits between the two ribbons in between two die pockets at the point of cut out. The wedge is typically heated in order to facilitate the sealing process, although for some forms of vegetarian based gelatin it is not. The wedge injection causes the two flat ribbons to expand into the die pockets, giving rise to the three-dimensional (3D) finished product. After encapsulation, the softgel capsules are dried for an extended period from a couple of days to weeks depending on the product.

Within the prior art printing, e.g. laser printing, on the surface of a soft capsule using a laser beam is carried out individually on a second manufacturing machine after the soft-gel capsules have been completely encapsulated and sufficiently dried. However, this method gives rise to several issues. Firstly, as the laser printing is performed only after sufficient drying then the total time, manufacturing cost, etc. become extremely significant. Further, as softgel capsules are usually elliptical in shape then they can be aligned within the separate laser printing equipment relatively easily. However, if the softgel capsule shapes cannot be easily aligned within the second laser printing machine then the position of the laser marking upon the softgel capsule is highly variable.

However, even where the softgel capsule is easily aligned within a laser marking equipment, such as with common 3D elliptical softgel capsules, which is separate to the softgel capsule manufacturing equipment then there exists the problem that the location on the softgel capsule may be aligned relative to the overall geometry but an absolute position on the softgel cannot be defined. For example, considering the 3D elliptical softgel capsules, the alignment can ensure that the laser marking is performed at a defined location along the long axis of the 3D elliptical softgel capsule but not at a defined point around the surface. This means that the laser marking may be either upon one of the two softgel shell portions entirely or across them both wherein the laser marking therefore crosses over one of the two sealing lines where the two softgel shell sheets are joined together. Accordingly, this can provide a degradation in the seal of the softgel capsule leading to either a complete failure of the softgel capsule or permitting ingress of materials from the external environment into the softgel capsule filling.

Accordingly, it would be beneficial to provide a means for laser marking the softgel capsules during their fabrication process such that the absolute position of the laser marking upon the softgel capsule relative to the overall external geometry and seals can be defined.

Further, as noted above within the prior art softgel capsules are formed using sheets of material comprising gelatin, water, an opacifier and a plasticizer. Accordingly, care must be taken to ensure that the opacifier and plasticizer either individually or in combination are themselves not detrimental to the user taking the pharmaceutical product or other product such as vitamins, supplements etc. within the softgel capsules. Further, the opacifier and plasticizer either individually or in combination should not combine with or react with the pharmaceutical product or other product within the softgel capsules leading to either degradation of the pharmaceutical product or other product or the formation of a byproduct which is toxic to the user.

Accordingly, it would be beneficial for either such gelatin sheets or only one gelatin sheet of the pair gelatin sheets to be laser marked during the manufacturing sequence of the softgel capsules to define the absolute positioning on the final softgel capsule product.

Other aspects and features of the present invention will become apparent to those ordinarily skilled in the art upon review of the following description of specific embodiments of the invention in conjunction with the accompanying figures.

SUMMARY

It is an object of the present invention to mitigate limitations within the prior art relating to softgel capsule manufacturing and more specifically to laser marking softgel capsules and encapsulated softgel capsules using gelatin, non-animal gelatin, tapioca starch, carrageenan, pea starch, and polymers during manufacturing.

In accordance with an embodiment of the invention there is provided a method comprising applying a laser marking to a sheet of material of a pair of sheets of material; forming a capsule from portions of the pair of sheets of material using a pair of die rollers; wherein each die roller of the pair of die rollers comprises a cavity allowing the capsule to be formed from the portions of the pair of sheets of material and a filler.

In accordance with an embodiment of the invention there is further provided a method comprising applying a laser marking to a sheet of material of a pair of sheets of material; forming a capsule from portions of the pair of sheets of material using a pair of die rollers; wherein each die roller of the pair of die rollers comprises a cavity allowing the capsule to be formed from the portions of the pair of sheets of material and a filler; wherein the location of the laser marking on the sheet of material of the pairs of sheets of material is established such that the laser marking does not overlap at least one of a seal or a joint between the pair of sheets of material formed during the formation of the capsule.

In accordance with an embodiment of the invention there is yet further provided a method comprising applying a laser marking to a sheet of material of a pair of sheets of material; forming a capsule from portions of the pair of sheets of material using a pair of die rollers; wherein each die roller of the pair of die rollers comprises a cavity allowing the capsule to be formed from the portions of the pair of sheets of material and a filler; wherein the location of the laser marking on the sheet of material of the pairs of sheets of material is established such that the laser marking is in a predetermined location upon the capsule relative to at least one of a seal or a joint between the pair of sheets of material formed during the formation of the capsule.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Figure 1:
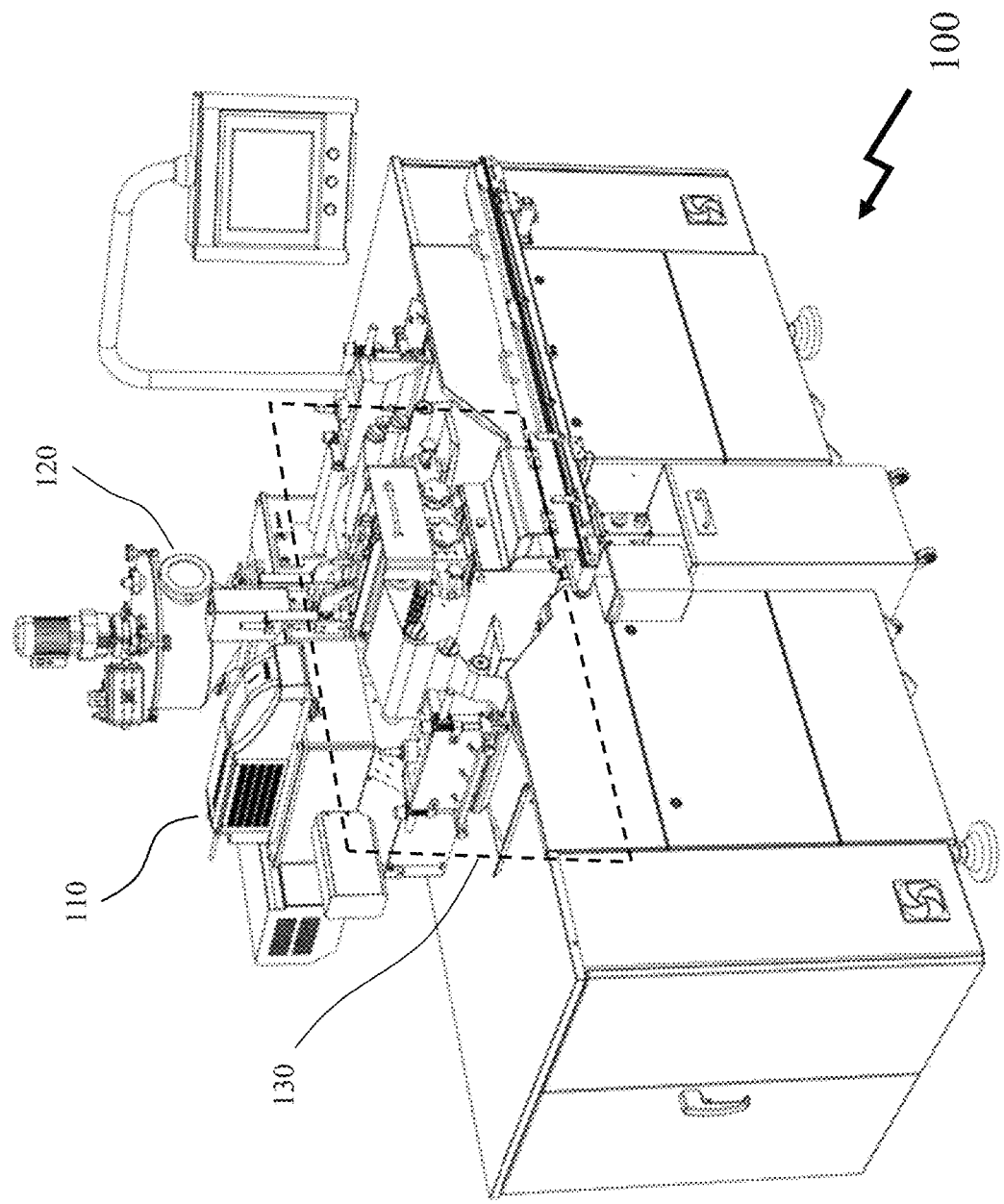
FIGS. 1 to 5 respectively depict a softgel manufacturing system exploiting a laser marking system according to an embodiment of the invention.

The present description is directed to softgel capsule manufacturing and more specifically to laser marking softgel capsules and encapsulated softgel capsules using gelatin, non-animal gelatin, tapioca starch, carrageenan, pea starch, and polymers during manufacturing.

The ensuing description provides representative embodiment(s) only, and is not intended to limit the scope, applicability or configuration of the disclosure. Rather, the ensuing description of the embodiment(s) will provide those skilled in the art with an enabling description for implementing an embodiment or embodiments of the invention. It being understood that various changes can be made in the function and arrangement of elements without departing from the spirit and scope as set forth in the appended claims. Accordingly, an embodiment is an example or implementation of the inventions and not the sole implementation. Various appearances of "one embodiment," "an embodiment" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention can also be implemented in a single embodiment or any combination of embodiments.

Reference in the specification to "one embodiment", "an embodiment", "some embodiments" or "other embodiments" means that a particular feature, structure, or characteristic described in connection with the embodiments is included in at least one embodiment, but not necessarily all embodiments, of the inventions. The phraseology and terminology employed herein is not to be construed as limiting but is for descriptive purpose only. It is to be understood that where the claims or specification refer to "a" or "an" element, such reference is not to be construed as there being only one of that element. It is to be understood that where the specification states that a component feature, structure, or characteristic "may", "might", "can" or "could" be included, that particular component, feature, structure, or characteristic is not required to be included.

Reference to terms such as "left", "right", "top", "bottom", "front" and "back" are intended for use in respect to the orientation of the particular feature, structure, or element within the figures depicting embodiments of the invention. It would be evident that such directional terminology with respect to the actual use of a device has no specific meaning as the device can be employed in a multiplicity of orientations by the user or users.

Reference to terms "including", "comprising", "consisting" and grammatical variants thereof do not preclude the addition of one or more components, features, steps, integers or groups thereof and that the terms are not to be construed as specifying components, features, steps or integers. Likewise, the phrase "consisting essentially of", and grammatical variants thereof, when used herein is not to be construed as excluding additional components, steps, features integers or groups thereof but rather that the additional features, integers, steps, components or groups thereof do not materially alter the basic and novel characteristics of the claimed composition, device or method. If the specification or claims refer to "an additional" element, that does not preclude there being more than one of the additional element.

Within the following descriptions with respect to embodiments of the invention a softgel capsule is described as comprising a shell (softgel shell) and a filler. The filler may include, for example, a pharmaceutical product, pharmaceutical products, a vitamin, vitamins, a supplement, supplements, a food, a seasoning, a cosmetic, or a general product such as an adhesive. The filler is typically in the form of a liquid, gel, powder, or combination thereof such as a suspension. The shell is described as being gelatin although embodiments of the invention may be applied to other shell materials such as those which are animal derived, gelatin with an opacifier and plasticizer, or plant derived. A plant derived shell material for example being one based upon starch.

Referring to FIG. 1 there is depicted a softgel manufacturing system (SGMS) 100 according to an embodiment of the invention comprising:

Laser Marking System (LAMKS) 110;
Filler Storage (FILSTOR) 120; and
Capsule Formation and Filling System (CAFOFIS) 130.

Figure 2A:
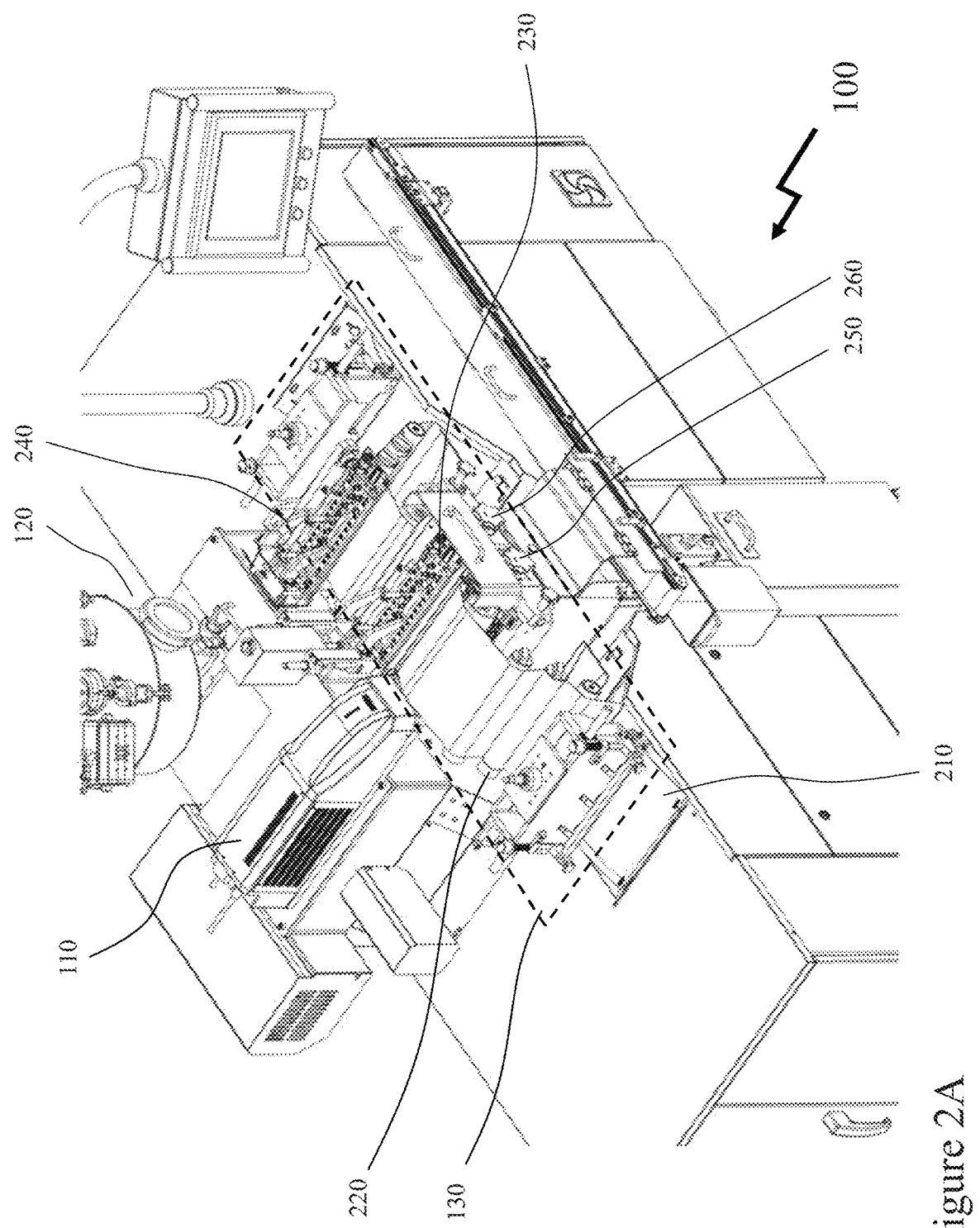
Figure 2B:
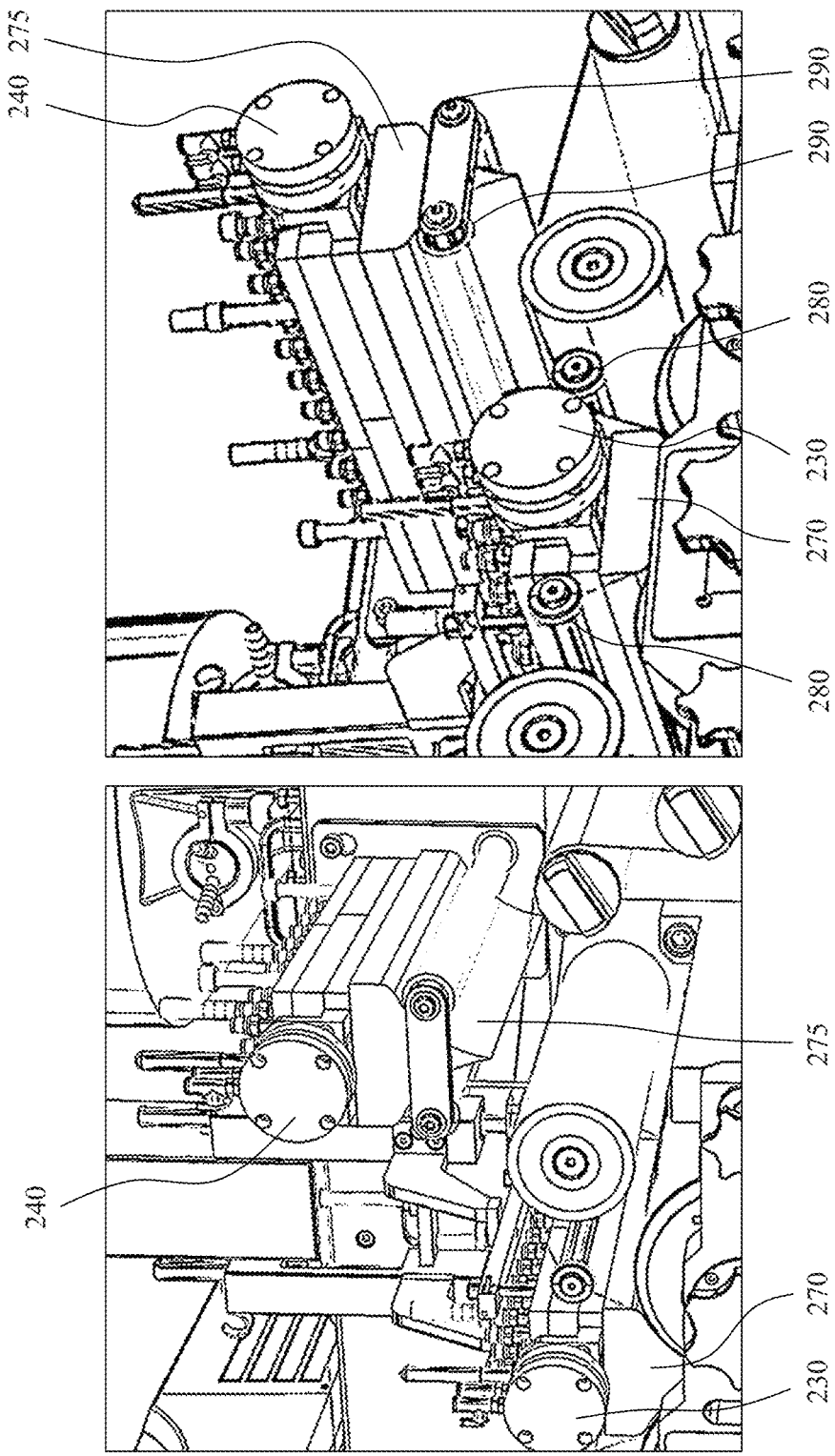

Referring to FIGS. 2A and 2B, the SGMS 100 is depicted from alternate perspectives comprising the LAMKS 110, FILSTOR 120 and CAFOFIS 130. The CAFOFIS 130 comprises a series of elements including rollers 220 which withdraw and position the softgel sheet (SGSheet) 210 relative to the Capsule Filler (CAPFIL) 230 which comprises a pair of rollers 280 together with heated wedge 270 which receives the filler from the FILSTOR 120 and delivers a defined amount of the filler at the right time and location between the die rollers within the SGMS 100 such that each pair of pockets (cavities) on the left and right DIEROLLS 250 and 260 respectively form a complete die. The SGSheet 210 is fed from either side of the CAPFIL 230 and fed down between the left and right DIEROLL 250 and 260 respectively, which provide the pair of cavities for forming the capsule, wherein the capsules are formed and sealed. Also depicted is a second CAPFIL 240 which comprises another pair of rollers 290 together with heated wedge 275. Typically, the SGMS 100 would employ the first CAPFIL 230 with the left and right DIEROLL 250 and 260 whilst the second CAPFIL 240 would be employed with a different pair of DIEROLL as the heated wedges 270 and 275 at the bottom of each of first and second CAPFIL 230 and 240 are designed in dependence upon the DIEROLL size.

However, within some alternate SGMS machine configurations the SGMS may comprise two FILSTOR and two CAPFIL wherein each FILSTOR is employed in dependence upon which CAPFIL is currently employed for capsule filling. For example, these may both dispense the same volume into the capsules whose size is defined by the cavities within the DIEROLLs allowing the SGMS to quickly be swapped from one filler to another without significant effort. Optionally, other CAPFILs and DIEROLLs may be employed with the SGMS 100 wherein a CAPFIL is, typically, associated with a specific matched pair of left and right DIEROLLs but may be associated with multiple pairs of DIEROLLs of similar dimensions such as producing alternate capsule geometries.

Figure 3:
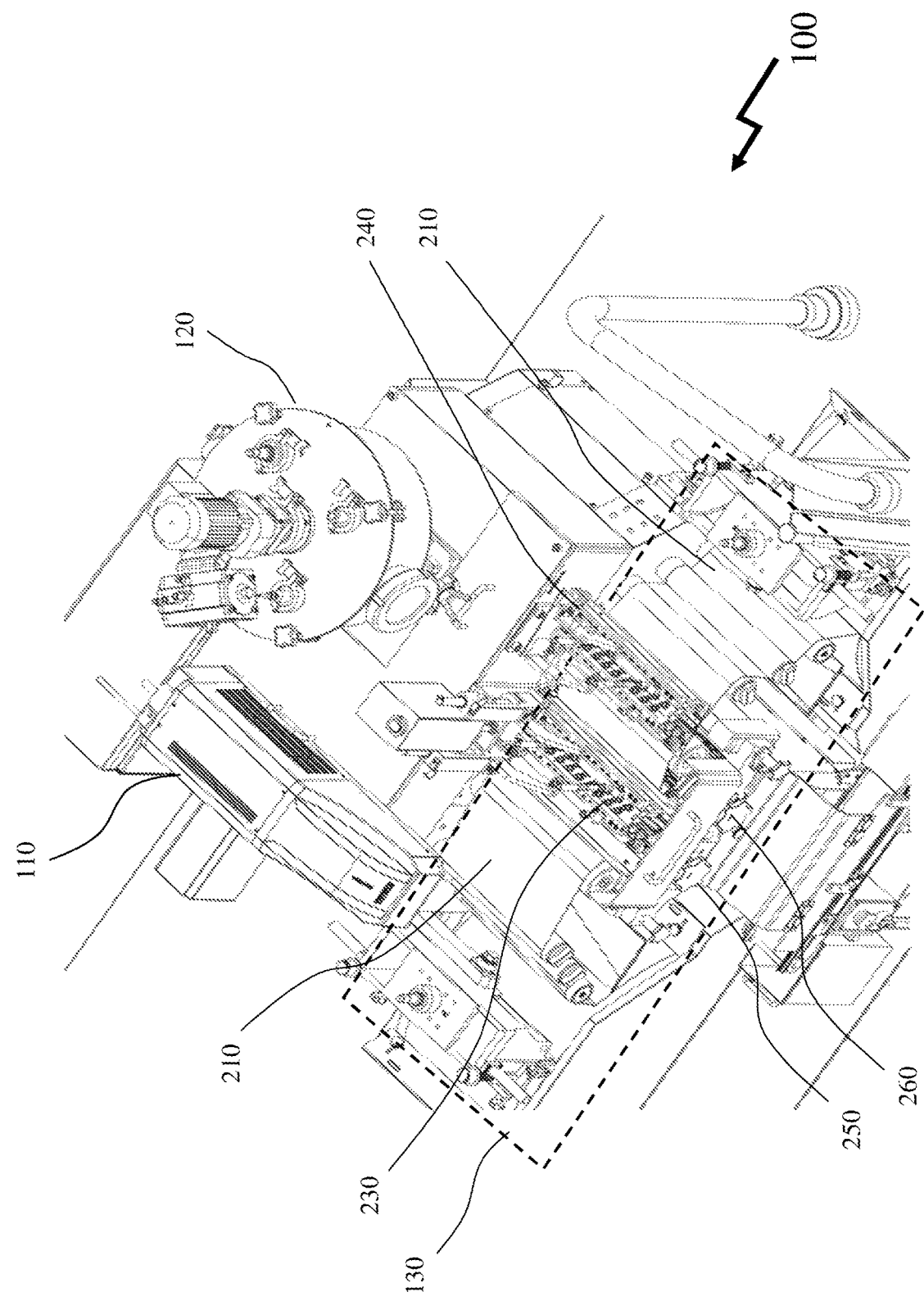

Now referring to FIG. 3 the SGMS 100 is depicted from an alternate perspective comprising the LAMKS 110, FILSTOR 120 and CAFOFIS 130. Also depicted are the SGSheet 210, first CAPFIL 230, left DIEROLL 250 and right DIEROLL 260.

Figure 4:
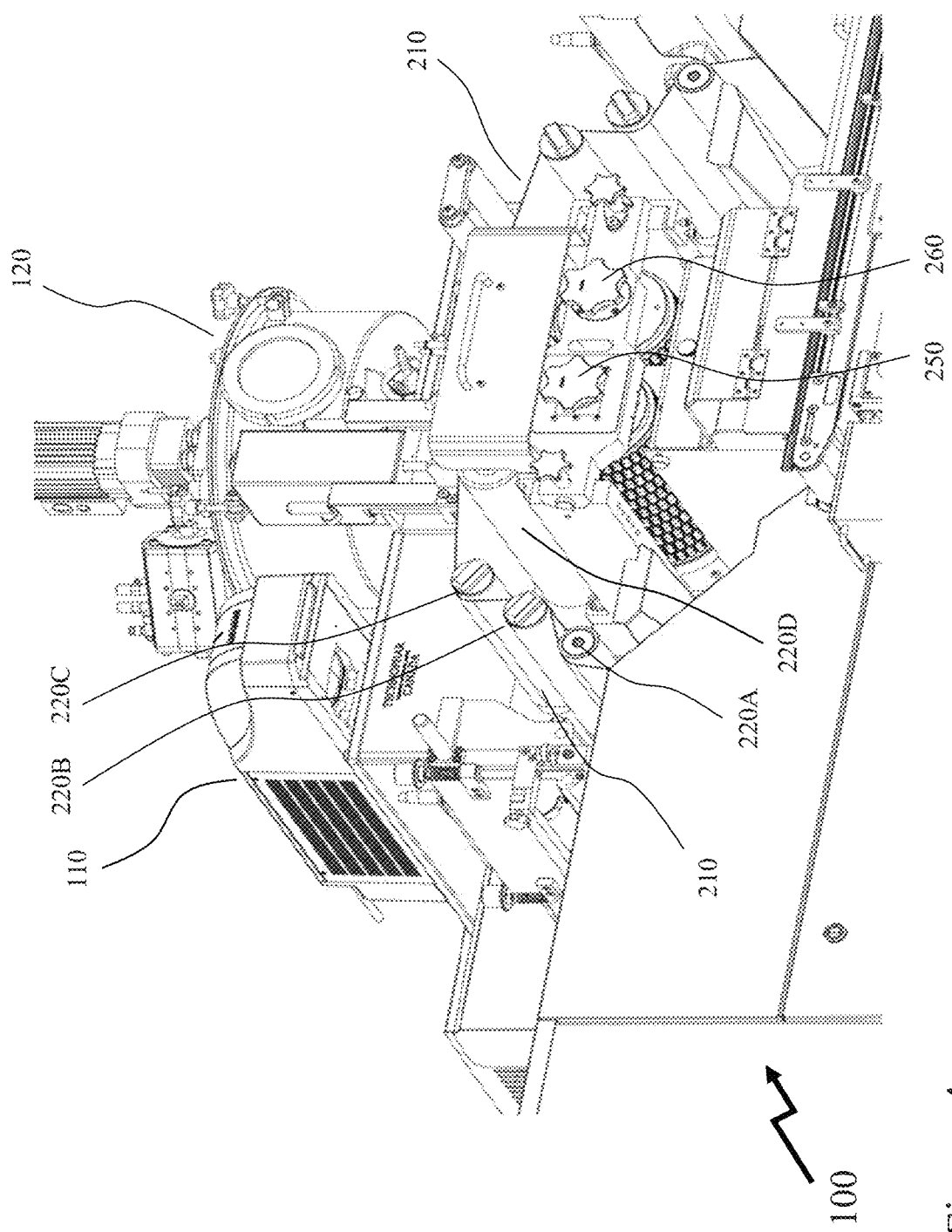

Referring to FIG. 4 the SGMS 100 is depicted from an alternate perspective comprising the LAMKS 110 and FILSTOR 120. Also depicted are the SGSheet 210, first CAPFIL 230, left DIEROLL 250 and right DIEROLL 260. Also depicted are the first to fourth rollers 220A to 220D on each side which guide and direct the SGSheet 210 to the appropriate positions between the first CAPFIL 230 and the left and right DIEROLLS 250 and 260 respectively and below the first CAPFIL 230.

Figure 5:
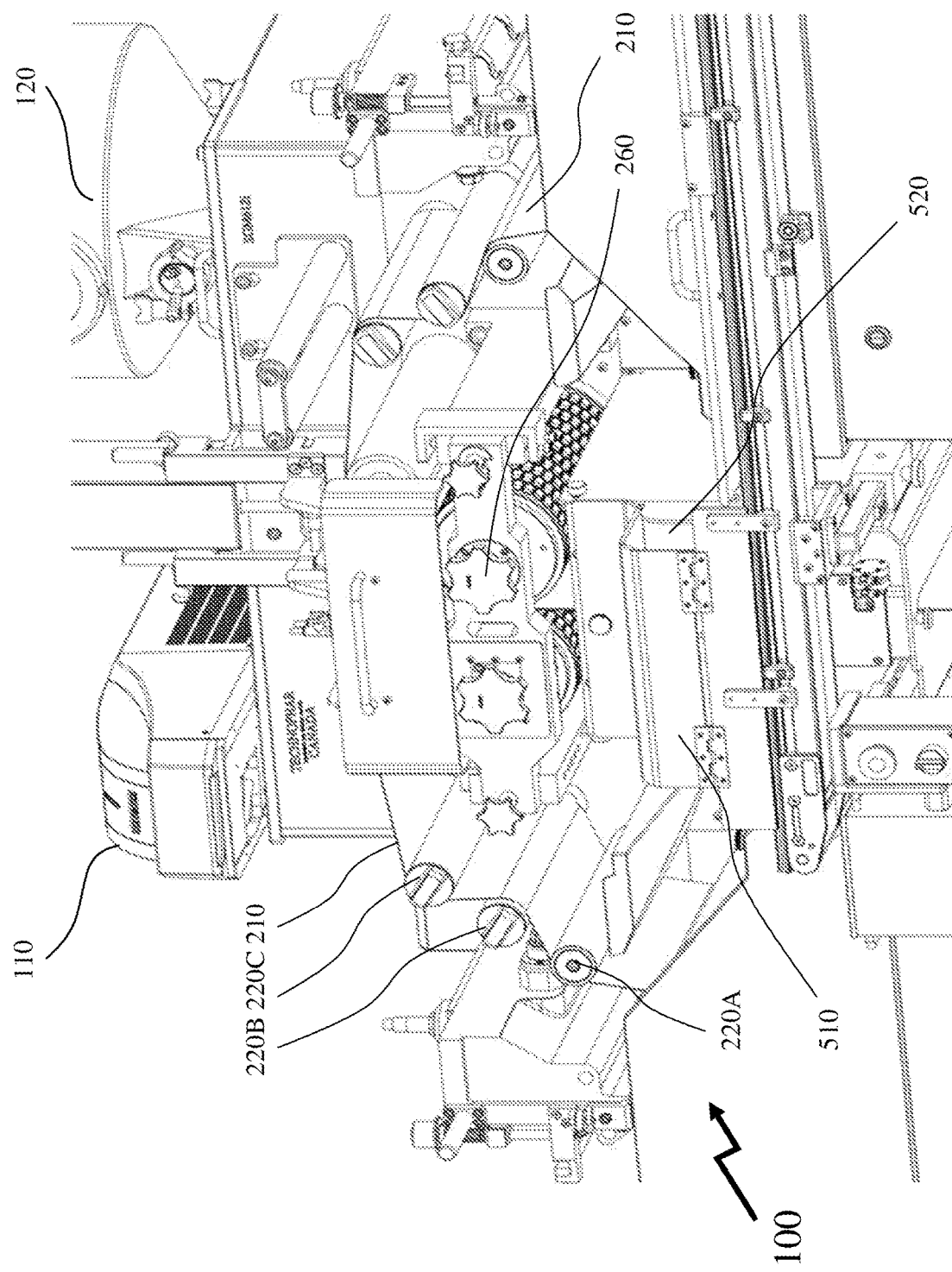

Referring to FIG. 5 the SGMS 100 is depicted from an alternate perspective comprising the LAMKS 110, FILSTOR 120 and CAFOFIS. Also depicted are the SGSheet 210, first CAPFIL 230, left DIEROLL 250 and right DIEROLL 260. Also depicted are first and second conveyors 510 and 520 which move the formed discrete capsules which drop down onto a third conveyor (not depicted) and transfer them to another system such as a storage bin, a capsule QA system, or a capsule packaging system for example.

Within FIGS. 1 to 5 respectively the SGMS 100 is depicted with the LAMKS 110 mounted to the upper left of the SGMS 100 wherein the laser marking is applied to the SGSheet 210 as it traverses the region between third roller 220C and fourth roller 220D before it goes down towards the left DIEROLL 250. Accordingly, in this configuration the SGMS 100 applies marking on one of the two SGSheets 210 that are employed to form the softgel capsule.

Figure 6:
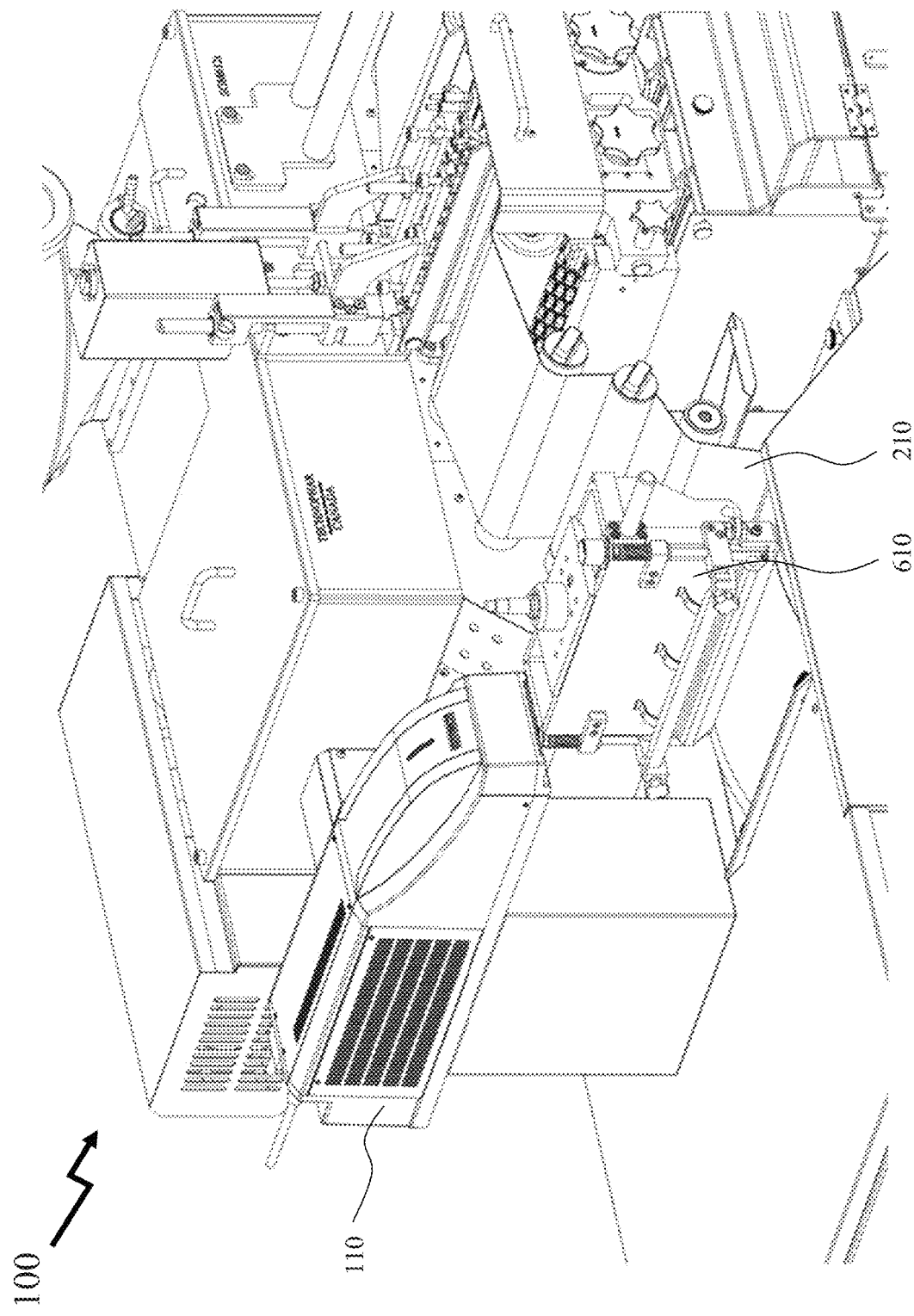
FIG. 6 depicts a softgel manufacturing system exploiting a laser marking system according to an embodiment of the invention.

However, referring to FIG. 6 the LAMKS 110 is depicted in a different position on an SGMS 100 wherein the SGSheet 210 is initially drawn from a Feeder 610 on the left hand side of the SGMS 100 before being fed through the rollers etc. A similar feeder and roller arrangement, which is not depicted, would be on the right hand side of the machine such as depicted in FIGS. 1 to 5 respectively.

However, it would be evident to one of skill in the art that whilst the SGMS 100 depicted in FIGS. 1 to 6 employs a single LAMKS 110 that other SGMS systems according to embodiments of the invention may employ two or more LAMKS systems. For example, dual LAMKS may be employed in order to laser mark each SGSheet 210, i.e. those on the left hand side of the machine and the right hand side of the machine. It would be evident that within other embodiments of the invention the one or more LAMKS may be positioned in alternate locations relative to the die rollers such that the film is marked prior to the formation of the softgel capsules. For example, the LAMKS 110 may be positioned within the body (frame) of the SGMS 100.

Within embodiments of the invention the LAMKS may be configured in location and with respect to the SGSheet such that the laser marking is applied to the surface of the SGSheet which will form the inner surface of the softgel capsule such that the external surface of the softgel capsule is not marked.

Within embodiments of the invention LAMKS may be configured in location and with respect to the SGSheet such that laser markings are applied to both surfaces of one or both of the SGSheets such that the laser markings are on both the inner and outer surfaces of the softgel capsule.

The SGMS depicted in FIGS. 1 to 6 exploit a pair of SGSheet forming units disposed on the left and right hand sides of the central filling and die roller portion of the SGMS. In operation these SGSheet forming units solidify and form the shell material, SGSheet, from an initial liquid state into a solid sheet. To achieve this the SGSheet forming units may comprise, for example, a spreader box, e.g. Feeder 610 in FIG. 6, which discharges the liquid outer shell material as a sheet state of a substantially constant thickness wherein a casting drum (not depicted within FIGS. 1 to 6 as it is internal to the SGMS cools the outer sheet discharged from the spreader box. According to the design of the SGSheet forming unit the SGSheet is formed into a sheet having an appropriate thickness while being gradually dried and cooled to an appropriate temperature before being fed through the series of rollers, e.g. first to fourth rollers 220A to 220D respectively in FIG. 4, to the central portion of the SGMS. As the SGSheet or SGSheets traverse from the SGSheet forming unit to the central portion one or both are marked with the one or more LAMKS. Optionally, within other embodiments of the invention the left and right SGSheet forming units may be omitted if prefabricated rolls of SGSheet material are employed and fed to the central unit, for example. Within embodiments of the invention the SGSheet itself is not monitored for temperature, although within other embodiments of the invention it may be, but the temperature(s) of the left DIEROLL 250 and/or right DIEROLL 260 are monitored.

Once the SGSheet has been laser marked then the SGSheets are moved from the SGSheet forming units to the central capsule forming portion of the SGMS. Here, the two SGSheets are brought together between rollers, e.g. left and right DIEROLL 250 and 260 respectively in FIG. 2, a predetermined volume of the filler is applied at locations where the cavities within the rollers will provide the softgel capsules. For example, an SGMS may form, for example, 1, 2, 4, 6, 8, 10, 12, 16, 20 softgel capsules in a row and have, for example, 1, 2, 3, 4, 5, 6 or more die cavities disposed around the periphery of the rollers. It would be evident that the number of softgel capsules in a row formed by the SGMS is a design choice. Similarly, the number of die cavities disposed around the periphery of the rollers is a design choice. Optionally, the die cavities on a roller may be linear rows or offset rows.

Within embodiments of the invention the spacing between sequentially applied laser markings along the SGSheet is determined in dependence upon the distance across the roller surface between sequential die cavities. Similarly, the lateral spacing between applied laser markings across the SGSheet is determined in dependence upon the positions of the die cavities along the length of the rollers.

Accordingly, it would be evident that the positioning of the laser markings on the SGSheets can be established such that the laser markings are on the sheet in locations that are within the die cavities when the SGSheet is fed through such that when the rollers come together the laser markings are not on the sealed edge(s) of the softgel capsules. Accordingly, in a manner where the filling through the CAPFIL 230 is synchronized with the rotation of the die rollers then the positions of the laser marking can be established and synchronized with the locations of the cavities within the die rollers such that the laser marking is in a predetermined position of the softgel capsule relative to the sealed edges.

Figure 7:
FIG. 7 depicts a fabricated softgel capsule using a softgel manufacturing system exploiting a laser marking system according to an embodiment of the invention wherein the laser marking is in a defined position relative to the sealed edges of the softgel capsule.

Referring to FIG. 7 there is depicted an image of a fabricated softgel capsule using a softgel manufacturing system exploiting a laser marking system according to an embodiment of the invention wherein the laser marking is in a defined position relative to the sealed edges of the softgel capsule.

Figure 8:
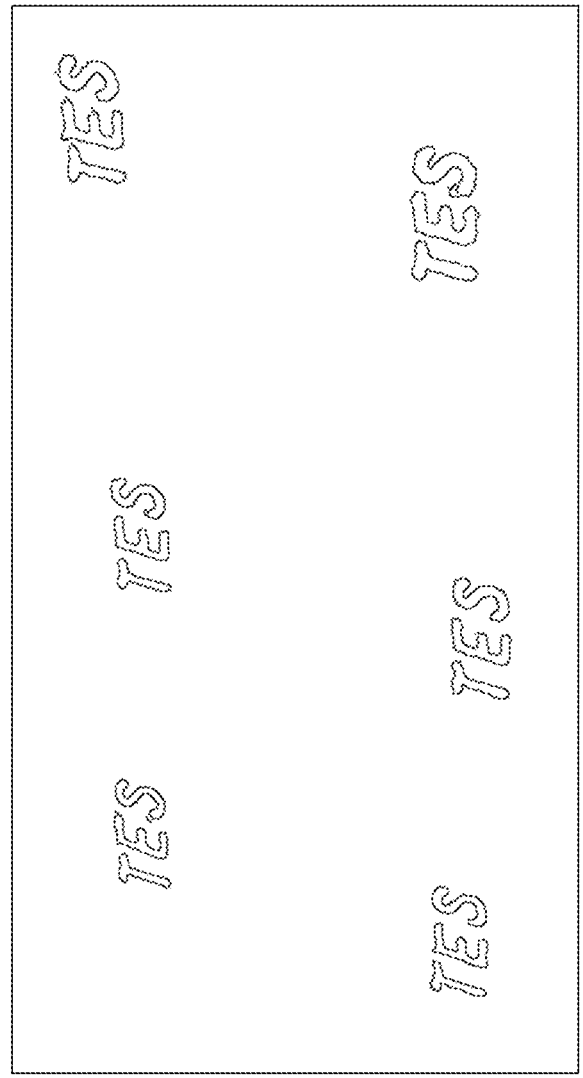
FIG. 8 depicts a softgel sheet with laser markings formed using a softgel manufacturing system exploiting a laser marking system according to an embodiment of the invention.

Referring to FIG. 8 there is depicted an image of a SGSheet with multiple laser markings as formed upon an SGMS according to an embodiment of the invention depicting multiple laser marking, in this instance the text "TES", laterally across the sheet and in multiple rows up across the sheet.

Figure 9:
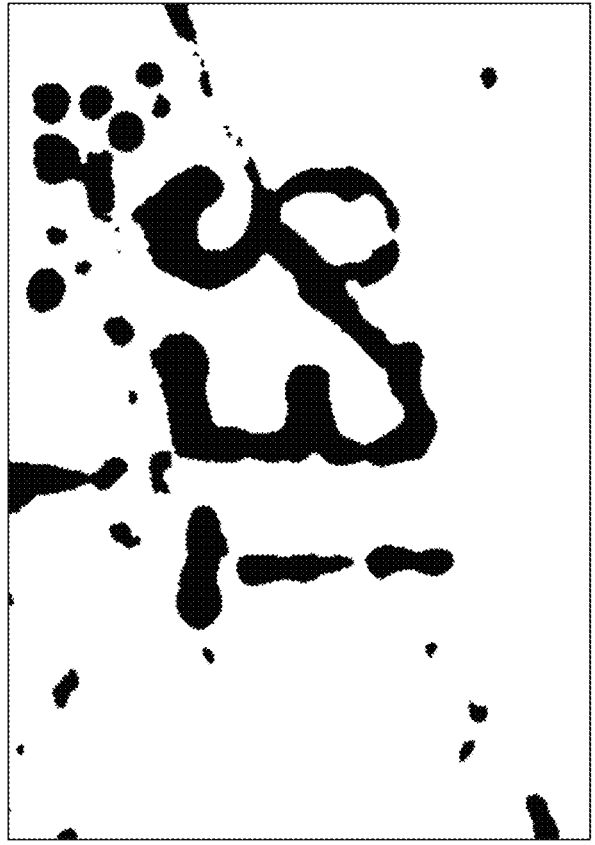
FIGS. 9 and 10 depict a softgel sheet with laser markings formed using a softgel manufacturing system exploiting a laser marking system according to an embodiment of the invention wherein the laser marked softgel sheet is entering the die rollers.
Figure 10:

Now referring to FIGS. 9 and 10 there are depicted images of a softgel sheet with laser markings formed using a softgel manufacturing system exploiting a laser marking system according to an embodiment of the invention wherein the laser marked softgel sheet is entering the die rollers.

Figure 11:
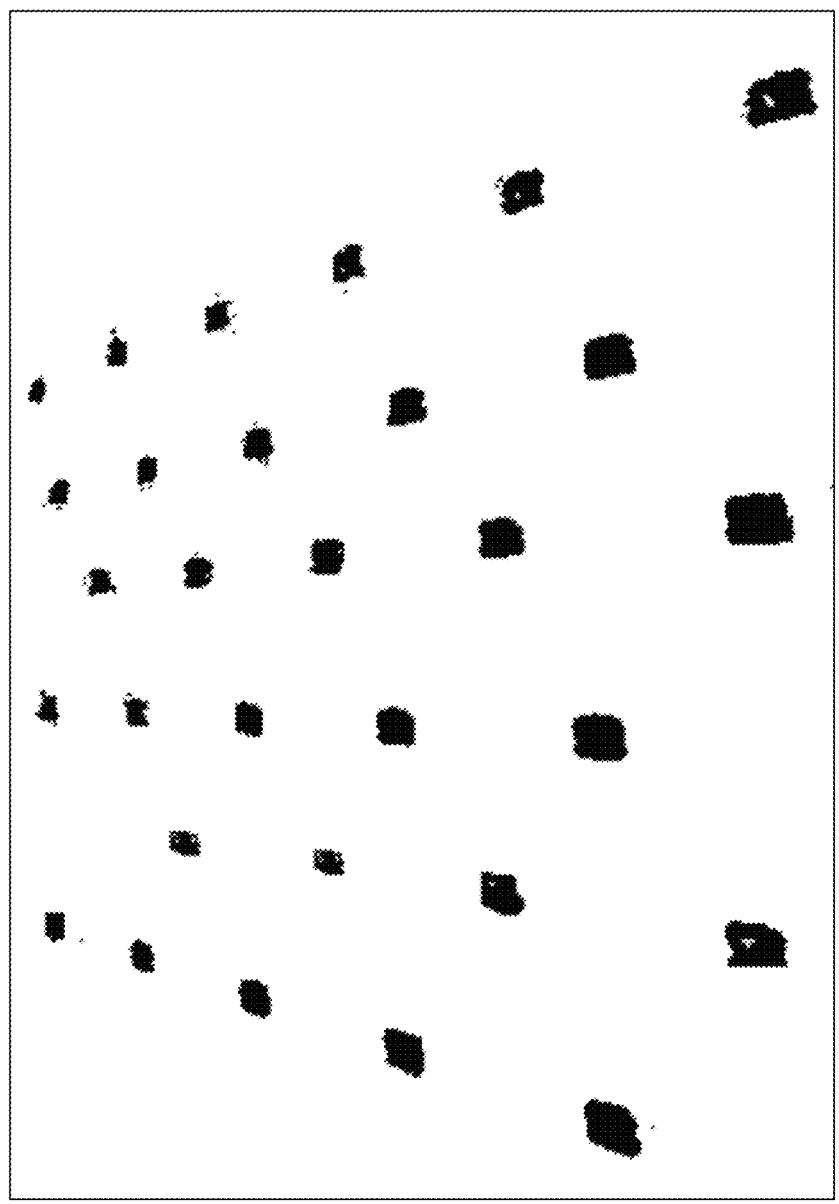
FIG. 11 depicts a softgel sheet with laser markings formed using a softgel manufacturing system exploiting a laser marking system according to an embodiment of the invention wherein the laser marked softgel sheet is entering the die rollers.
Figure 12:
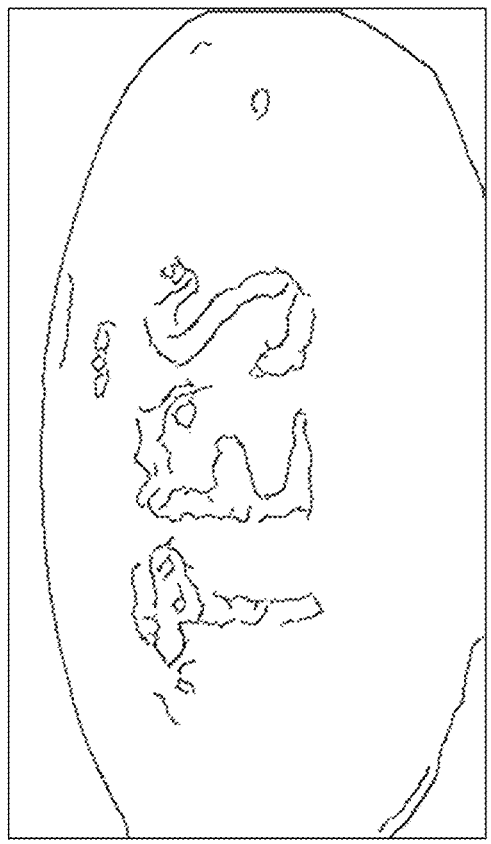
FIGS. 12 to 15 depict fabricated softgel capsules using a softgel manufacturing system exploiting a laser marking system according to an embodiment of the invention wherein the laser marking is in a defined position relative to the sealed edges of the softgel capsule.
Figure 13:
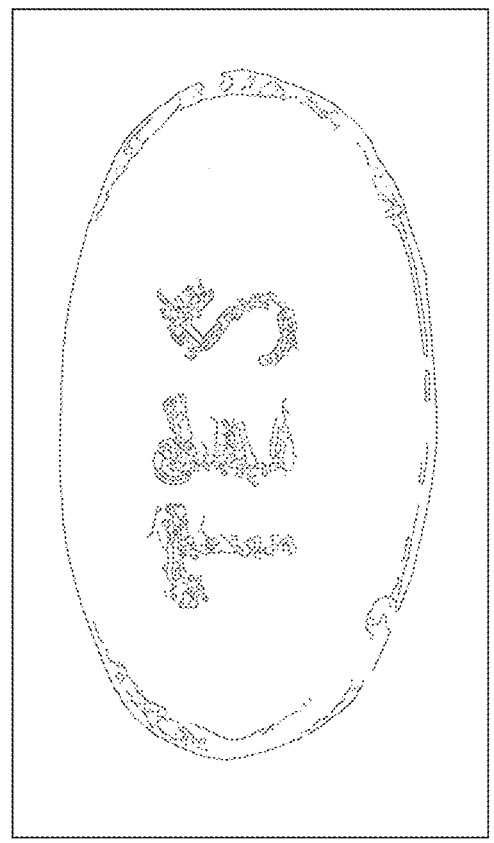
Figure 14:
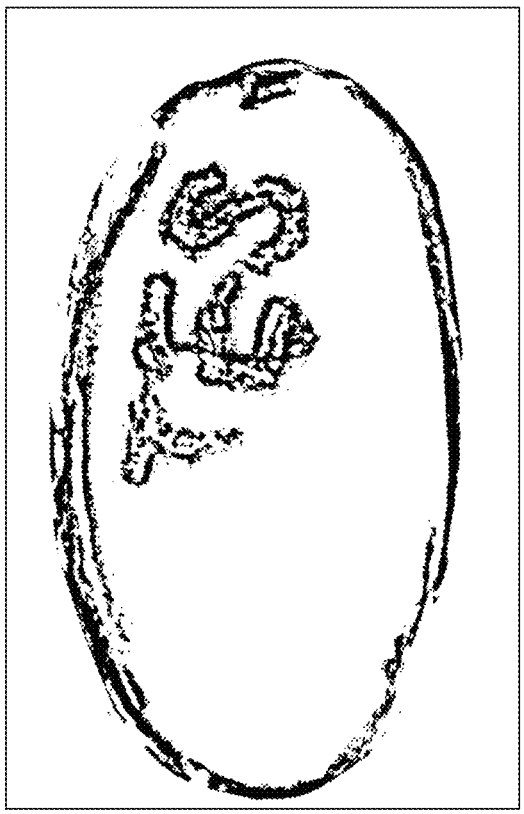
Figure 15:
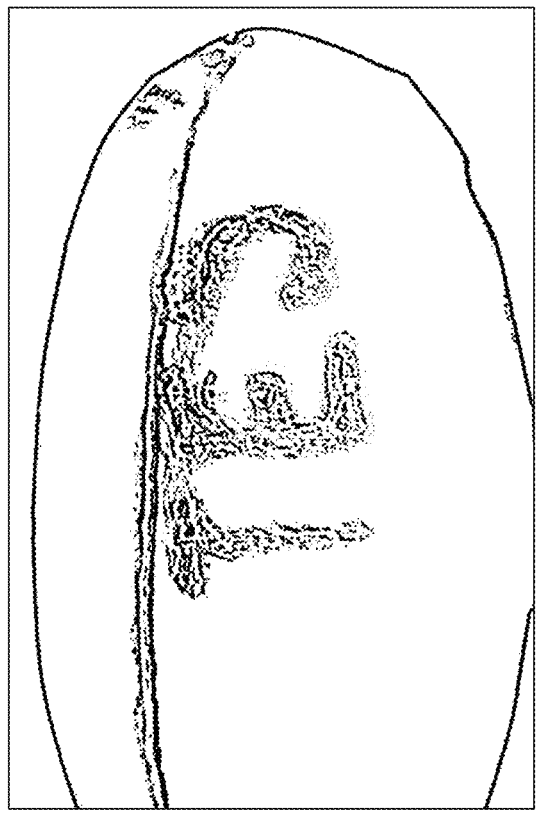

Referring to FIG. 11 there is depicted a softgel sheet with laser markings formed using a softgel manufacturing system exploiting a laser marking system according to an embodiment of the invention wherein the laser marked softgel sheet is entering the die rollers.

Now referring to FIGS. 12 to 15 there are depicted fabricated softgel capsules using a softgel manufacturing system exploiting a laser marking system according to an embodiment of the invention wherein the laser marking is in a defined position relative to the sealed edges of the softgel capsule.

Referring to Table 1 below there are exemplary settings for SGMS machines according to embodiments of the invention exploiting laser marking.

TABLE 1

| Exemplary Machine Settings | | | | |
|---|---|---|---|---|
| Die Roll Speed | MR Speed | Drum Speed | NextGen Drum Speed | Oil Roll Speed |
| 1.00 | 4.17 | 0.21 | 0.30 | 2.86 |
| 2.00 | 8.33 | 0.43 | 0.59 | 5.73 |
| 3.00 | 12.50 | 0.64 | 0.89 | 8.59 |
| 4.00 | 16.67 | 0.85 | 1.19 | 11.45 |
| 5.00 | 20.83 | 1.07 | 1.48 | 14.31 |
| 6.00 | 25.00 | 1.28 | 1.78 | 17.18 |
| 7.00 | 29.17 | 1.49 | 2.08 | 20.04 |
| 8.00 | 33.33 | 1.70 | 2.37 | 22.90 |
| 9.00 | 37.50 | 1.92 | 2.67 | 25.76 |
| 10.00 | 41.67 | 2.13 | 2.96 | 28.63 |
| 11.00 | 45.83 | 2.34 | 3.26 | 31.49 |
| 12.00 | 50.00 | 2.56 | 3.56 | 34.35 |
| 13.00 | 54.17 | 2.77 | 3.85 | 37.21 |
| 14.00 | 58.33 | 2.98 | 4.15 | 40.08 |
| 15.00 | 62.50 | 3.20 | 4.45 | 42.94 |
| 16.00 | 66.67 | 3.41 | 4.74 | 45.80 |
| 17.00 | 70.83 | 3.62 | 5.04 | 48.66 |
| 18.00 | 75.00 | 3.84 | 5.34 | 51.53 |
| 19.00 | 79.17 | 4.05 | 5.63 | 54.39 |
| 20.00 | 83.33 | 4.26 | 5.93 | 57.25 |
| 21.00 | 87.50 | 4.47 | 6.23 | 60.11 |
| 22.00 | 91.67 | 4.69 | 6.52 | 62.98 |
| 23.00 | 95.83 | 4.90 | 6.82 | 65.84 |
| 24.00 | 100.00 | 5.11 | 7.11 | 68.70 |
| 25.00 | 104.17 | 5.33 | 7.41 | 71.56 |
| 26.00 | 108.33 | 5.54 | 7.71 | 74.43 |
| 27.00 | 112.50 | 5.75 | 8.00 | 77.29 |
| 28.00 | 116.67 | 5.97 | 8.30 | 80.15 |
| 29.00 | 120.83 | 6.18 | 8.60 | 83.02 |
| 30.00 | 125.00 | 6.39 | 8.89 | 85.88 |

Within embodiments of the invention the SGSheet has been described and depicted as being gelatin based. This animal gelatin may be derived from beef bones, beef hide, pork skin, and fish for example. Within other embodiments of the invention the SGSheet may be a natural film formed from carrageenan/starch, tapioca (cassava root), and pea starch. Within other embodiments of the invention the SGSheet may be a polymer.

Whilst the embodiments of the invention depicted in respect of FIGS. 1 to 6 are based upon a standard commercial 612i softgel capsule manufacturing system manufactured by Technophar the embodiments of the invention may be employed upon a wide range of existing and new SGMS systems with SGSheet widths for example ranging from 25 mm to 760 mm (1 inch to 30 inches).

Further, whilst FIGS. 7 and 12-15 depict elliptical softgel capsules embodiments of the invention may be applied to other capsule geometries including, but not limited to, round capsules (essentially section of a cylinder), square or oblong capsules (essentially section of a rectangular or square cuboid), triangular capsules (essentially a section of a triangular prism), spherical capsules, oval capsules (prolate spheroid), oblate spheroid, a regular three-dimensional polygon, an irregular three-dimensional polygon, and a specialty capsule shape. However, in each instance the laser markings may be applied to the SGSheet during capsule manufacturing such that the laser marking is in a defined physical position on the capsule and in a defined location relative to a sealed edge of the capsule.

The volume of a softgel capsule formed according to embodiments of the invention may, for example, support a fill volume of filler ranging from 0.20 mg to 10,000 mg although other volumes may be supported.

The laser marking system employed in providing prototype laser marking as depicted in FIGS. 7 and 12-15 employs a carbon dioxide ($CO_2$) laser system which can, according to the composition of the SGSheet, be employed to ablate the surface of the SGSheet or locally heat the SGSheet to create microbubbles/microdefects. Optionally, according to the desired format of the laser marking and the composition of the SGSheet other lasers may be employed as are known in the art.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method of forming a capsule comprising:
   applying a laser marking to a sheet of material of a pair of sheets of material; and
   forming a capsule from portions of the pair of sheets of material using a pair of die rollers or another pair of die rollers; wherein
   each die roller of the pair of die rollers or the another pair of die rollers comprises a cavity allowing the capsule to be formed from the portions of the pair of sheets of material and a filler;
   the formation of the capsule from the portions of the pair of sheets of material using the pair of die rollers or the another pair of die rollers employs a capsule filling system;
   the capsule filling system comprises:
   a first capsule filler comprising a first set of dispensers for the first capsule filler and a first heated wedge;
   a first roller pair comprising the pair of die rollers for use with the first capsule filler;
   a second capsule filler comprising a second heated wedge;
   a second roller pair comprising the another pair of die rollers for use with the second capsule filler; wherein
   the capsule filling system employs the first capsule filler that can be swapped for the second capsule filler;
   the first capsule filler dispenses a volume of filler into capsules having a first capsule size and the second capsule filler dispenses a volume of filler into capsules having a second capsule size, each said first capsule size and said second capsule size being defined by cavities in the pair of die rollers and the another pair of die rollers, respectively; and
   a laser marking system configured for marking the sheet of material of the pair of sheets of material prior to the formation of the capsules of different sizes.

2. The method of claim 1, further including
   the first capsule filler employs a filler in the form of at least one of a liquid, a gel and a powder;
   the second capsule filler employs another filler in the form of at least one of a liquid, a gel and a powder; and
   the laser marking system is configured for marking the sheet of material of the pair of sheets of material prior to reaching the first capsule filler and the second capsule filler.

3. The method of claim 1, further including
   applying another laser marking to another sheet of material of the pair of sheets of material; wherein
   the location of the laser marking on the sheet of material of the pair of sheets of material is established such that the laser marking is in a predetermined location upon the capsule relative to at least one of a seal or a joint between the pair of sheets of material formed during the formation of the capsule; and
   the location of the another laser marking on the another sheet of material of the pair of sheets of material is established such that the another laser marking is in a predetermined location upon the capsule relative to at least one of a seal or a joint between the pair of sheets of material formed during the formation of the capsule.

4. The method of claim 3, further including
   the laser marking is on a side of the sheet of material of the pair of sheets of material such that the laser marking is on an inner surface of the formed capsule; and
   the another laser marking is on a side of the another sheet of material of the pair of sheets of material such that the another laser marking is on an inner surface of the formed capsule.

5. The method of claim 3, further including
   the laser marking is on a side of the sheet of material of the pair of sheets of material such that the laser marking is on an inner surface of the formed capsule; and
   the another laser marking is on a side of the another sheet of material of the pair of sheets of material such that the another laser marking is on an outer surface of the formed capsule.

6. The method of claim 3, further including
   the laser marking is on a side of the sheet of material of the pair of sheets of material such that the laser marking is on an inner surface of the formed capsule; and the another laser marking is on a side of the another sheet of material of the pair of sheets of material such that the another laser marking is on an outer surface of the formed capsule.

7. The method of claim 3, further including
applying an extra laser marking to the another sheet of material of the pair of sheets of material; and
applying a further laser marking to the another sheet of material of the pair of sheets of material, wherein
the location of the further laser marking on the another sheet of material of the pair of sheets of material is established such that the further laser marking is in a predetermined location upon the capsule relative to at least one of a seal or a joint between the pair of sheets of material formed during the formation of the capsule;
the location of the extra laser marking on the another sheet of material of the pair of sheets of material is established such that the extra laser marking is in a predetermined location upon the capsule relative to at least one of a seal or a joint between the pair of sheets of material formed during the formation of the capsule;
the further laser marking is on a side of the another sheet of material of the pair of sheets of material such that the further laser marking is on an inner surface of the formed capsule; and
the extra laser marking is on another side of the another sheet of material of the pair of sheets of material such that the extra laser marking is on an outer surface of the formed capsule.

8. The method of claim 1, further including
the pair of die rollers and the another pair of die rollers being different sizes; wherein
the first heated wedge and the second heated wedge are sized as a function of the size of the pair of die rollers and the another pair of die rollers, respectively.

9. A method of forming a capsule comprising:
applying a laser marking to a sheet of material of a pair of sheets of material; and
forming a capsule from portions of the pair of sheets of material using a pair of die rollers or another pair of die rollers; wherein
each die roller of the pair of die rollers or the another pair of die rollers comprises a cavity allowing the capsule to be formed from the portions of the pair of sheets of material and a filler;
the formation of the capsule from the portions of the pair of sheets of material using the pair of die rollers or the another pair of die rollers employs a capsule filling system;
the capsule filling system comprises:
  a first capsule filler comprising a first set of dispensers for the first capsule filler and a first heated wedge;
  a first roller pair comprising the pair of die rollers for use with the first capsule filler;
  a second capsule filler comprising a second heated wedge;
  a second roller pair comprising the another pair of die rollers for use with the second capsule filler; wherein
the capsule filling system employs the first capsule filler that can be swapped for the second capsule filler;
the first capsule filler employs a filler in the form of at least one of a liquid, a gel and a powder;
the second capsule filler employs another filler in the form of at least one of a liquid, a gel and a powder; and
a laser marking system configured for marking the sheet of material of the pair of sheets of material prior to the formation of the capsules of different sizes.

10. The method of claim 9, further including
the pair of die rollers and the another pair of die rollers being different sizes; and
the first heated wedge and the second heated wedge are sized as a function of the size of the pair of die rollers and the another pair of die rollers, respectively.

11. A method of forming a capsule comprising:
applying a laser marking to a sheet of material of a pair of sheets of material; and
forming a capsule from portions of the pair of sheets of material using a pair of die rollers or another pair of die rollers; wherein
each die roller of the pair of die rollers or the another pair of die rollers comprises a cavity allowing the capsule to be formed from the portions of the pair of sheets of material and a filler;
the formation of the capsule from the portions of the pair of sheets of material using the pair of die rollers or the another pair of die rollers employs a capsule filling system;
the capsule filling system comprises:
  a first capsule filler comprising a first set of dispensers for the first capsule filler and a first heated wedge;
  a first roller pair comprising the pair of die rollers for use with the first capsule filler;
  a second capsule filler comprising a second heated wedge;
  a second roller pair comprising the another pair of die rollers for use with the second capsule filler; wherein
the capsule filling system employs the first capsule filler that can be swapped for the second capsule filler;
applying another laser marking to another sheet of material of the pair of sheets of material; wherein
the location of the laser marking on the sheet of material of the pair of sheets of material is established such that the laser marking is in a predetermined location upon the capsule relative to at least one of a seal or a joint between the pair of sheets of material formed during the formation of the capsule;
the location of the another laser marking on the another sheet of material of the pair of sheets of material is established such that the another laser marking is in a predetermined location upon the capsule relative to at least one of a seal or a joint between the pair of sheets of material formed during the formation of the capsule;
applying an extra laser marking to the another sheet of material of the pair of sheets of material;
applying a further laser marking to the another sheet of material of the pair of sheets of material, wherein
the location of the further laser marking on the another sheet of material of the pair of sheets of material is established such that the further laser marking is in a predetermined location upon the capsule relative to at least one of a seal or a joint between the pair of sheets of material formed during the formation of the capsule;
the location of the extra laser marking on the another sheet of material of the pair of sheets of material is established such that the extra laser marking is in a predetermined location upon the capsule relative to at least one of a seal or a joint between the pair of sheets of material formed during the formation of the capsule;
the further laser marking is on a side of the another sheet of material of the pair of sheets of material such that the further laser marking is on an inner surface of the formed capsule; and the extra laser marking is on another side of the another sheet of material of the pair of sheets of material such that the extra laser marking is on an outer surface of the formed capsule.

\* \* \* \* \*